United States Patent [19]

Manaka

[11] Patent Number: 4,740,387
[45] Date of Patent: Apr. 26, 1988

[54] LOW POWER GAS DETECTOR

[75] Inventor: Junji Manaka, Kawasaki, Japan

[73] Assignee: Ricoh Company Ltd., Japan

[21] Appl. No.: 838,289

[22] Filed: Mar. 10, 1986

Related U.S. Application Data

[62] Division of Ser. No. 577,858, Feb. 7, 1984, Pat. No. 4,580,439.

[30] Foreign Application Priority Data

Feb. 7, 1983 [JP] Japan .................................. 58-17381
Apr. 6, 1983 [JP] Japan .................................. 58-59179
Sep. 13, 1983 [JP] Japan ................................. 58-167472

[51] Int. Cl.⁴ ............................................. B05D 5/12
[52] U.S. Cl. .................................... 427/125; 427/123;
427/126.3; 427/126.5; 427/226; 427/87;
148/6.27; 437/143; 437/141
[58] Field of Search ...................... 427/125, 123, 126.3,
427/126.5, 87, 226, 101, 108; 148/6.27

[56] References Cited

U.S. PATENT DOCUMENTS

| | | | |
|---|---|---|---|
| 4,052,271 | 10/1977 | Beer | 204/38 A |
| 4,342,792 | 8/1982 | Brown | 427/376.4 |
| 4,362,765 | 12/1982 | Abe | 427/87 |
| 4,614,669 | 9/1986 | Yannopoulos | 427/126.3 |

Primary Examiner—Shrive P. Beck
Assistant Examiner—Vi Duong Dang
Attorney, Agent, or Firm—Guy W. Shoup

[57] ABSTRACT

A gas detector includes a gas detecting element comprised of a metal oxide semiconductor material which changes its value of electrical resistance at an elevated temperature when it absorbs a gas. In one form, the gas detecting element is supported in the form of a bridge so as to increase its response speed by making thermal capacity as small as possible. In another form, the gas detecting element is supported in the form a cantilever, more preferably in the form of a ring as formed along the periphery of a overhang portion of a disc-shaped layer of electrically insulating material. Also provided is a process for manufacturing a thin film of metal oxide, which may be advantageously used as a gas detecting element of a gas detector or a transparent electrode, for example, in a liquid crystal panel.

6 Claims, 15 Drawing Sheets

LOW POWER GAS DETECTOR

This is a divisional application based on copending application Ser. No. 577,858 filed Feb. 7, 1984 now U.S. Pat. No. 4,580,439.

BACKGROUND OF THE INVENTION

1. Field of the Invention

This invention relates to a gas detector for detecting the presence of a particular gas such as a combustible gas and a hazardous gas beyond a certain level and a method for manufacturing the same. In particular, the present invention relates to a low power gas detector of the semiconductor type suited for use as a gas leak alarm for detecting the presence of excessive amount of gas such as LP gas and commercial or utility gas and giving a warning signal upon detection. More specifically, the present invention relates to a method for manufacturing a metal oxide thin film which may be advantageously used as a gas detecting element in a semiconductor type gas detector or a transparent electrode film in a display panel or photoelectric sensor.

2. Description of the Prior Art

A gas detector using a metal oxide semiconductor such as $SnO_2$ and $ZnO$ is well known. In such a prior art gas detector, electrodes and/or coil-shaped electrodes also serving as heater coils are provided as buried in the body of metal oxide semiconductor, wherein changes in the resistance of the metal oxide semiconductor due to absorption of a particular gas at the surface are used to detect the presence or overamount of a particular gas. However, one of the particular disadvantages in the prior art gas detector has been the large power requirement. For example, none of the prior art gas detectors has been suited for use with batteries. Thus, there has been a need for developing a low power gas detector which may be driven by batteries for an extended period of time.

As a gas detecting element of a semiconductor type gas detector, use has been commonly made of a sintered metal oxide semiconductor. As described in the Japanese Patent Laid-open Publication No. 58-30648, the typical method for manufacturing such a gas detecting element is to produce tin oxide by processing tin with dense nitric acid and then a sediment of tin oxide thus obtained is sintered using a binder such as $SiO_2$ and $Al_2O_3$. However, as described above, instead of the prior art gas detector driven by a commercial line voltage, research has been and still is being carried out to develop a battery-driven gas detector. Under the circumstances, it is required to develop a gas detector smaller in scale and thus lower in power consumption. In such a miniaturized gas detector, a gas detecting element as thin as a few microns and as small in area as some hundreds of microns squared must be fabricated. None of the prior art techniques is capable of fabricating such a small-sized gas detecting element.

SUMMARY OF THE INVENTION

It is therefore a primary object of the present invention to provide an improved gas detector and a method for manufacturing the same.

Another object of the present invention is to provide an improved semiconductor type gas detector.

A further object of the present invention is to provide a battery-driven gas detector which is low in power consumption and small in size.

A still further object of the present invention is to provide a high-sensitivity gas detector excellent and stable in operation and long in service life.

A still further object of the present invention is to provide a gas detector which is suited for mass production and thus remarkably low in unit cost.

A still further object of the present invention is to provide a method of forming a desired pattern of metal oxide semiconductor film which is particularly suited for use as a gas detecting element or a transparent electrode film.

A still further object of the present invention is to provide a method of forming a film of metal oxide semiconductor having an extremely fine pattern.

Other objects, advantages and novel features of the present invention will become apparent from the following detailed description of the invention when considered in conjunction with the accompanying drawings.

BRIEF DESCRIPTION OF THE DRAWINGS

FIGS. 7 through 14 show steps of a process for manufacturing the gas detector 10 of FIG. 1 in accordance with one embodiment of the present invention wherein FIGS. 7, 9, 10, 12, 13 and 14 are cross-sectional views of the structure at each step and FIGS. 8 and 11 are plan views showing photo-mask patterns used during the process;

DESCRIPTION OF THE PREFERRED EMBODIMENTS

Figure 1:
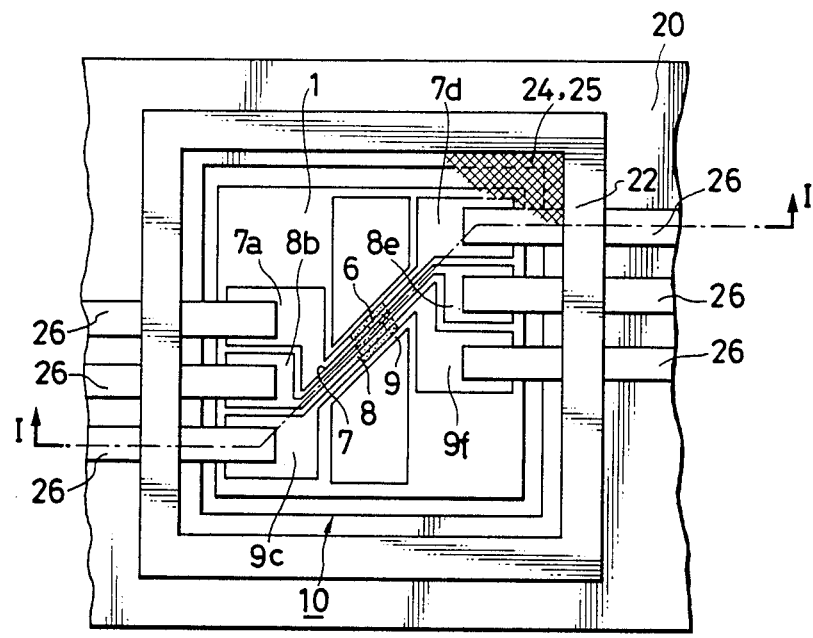
FIG. 1 is a plan view showing a gas detector constructed in accordance with one embodiment of the present invention.
Figure 2:
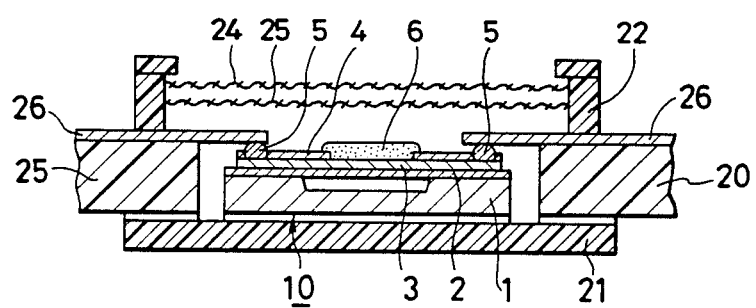
FIG. 2 is a cross-sectional view taken along line I—I shown in FIG. 1.

Referring now to FIG. 1, there is shown the overall structure of a gas detector 10 constructed in accordance with one embodiment of the present invention as mounted in a supporting structure. FIG. 2 is a cross-sectional view taken along line I—I indicated in FIG. 1. The gas detector 10 of the present invention generally comprises a substrate 1, an insulating layer 2 and a metal layer 3. The metal layer 3, in fact, is patterned into three strips 7, 8 and 9 arranged side by side, each including an elongated section and a pair of electrode or pad sections provided on both ends of the elongated section. Among these three strips, the elongated sections of the strips 7 and 9 serve as heaters with the sections 7a, 7d, 9c and 9f serving as pads, and the elongated section of the strip 8 serves as a gas detecting element with the sections 8b and 8e serving as pads thereof. The gas detector 10 also includes a gas detecting semiconductor layer 6 and an insulating layer 4. In registry in location with the electrode sections 7a, 8b, 9c, 7d, 8e and 9f, there are provided holes in the insulating layer 4 and bumps 5 are formed in the holes.

As best shown in FIG. 2, the gas detector 10 is mounted on a supporting structure, or film carrier 20 in the illustrated embodiment, with the bumps 5 of the electrode sections 7a, 8b, 9c, 7d, 8e and 9f bonded by thermocompression to respective leads 26 projecting from the film carrier 20. The gas detector 10 is covered by an anti-explosion net 24 and a dust-off filter 25 at its top and by a bottom cover 21 at its bottom. Thus, the gas detector 10 is provided as effectively enclosed. The anti-explosion net 24 and the dust-off filter 25 are fixedly attached to a top cover frame 22 which in turn is fixedly mounted on the film carrier 20 and they allow passage of gas therethrough. The dust-off filter 25 is provided so as to prevent the gas detector 10 from malfunctioning due to deposition of debris and foreign matter on the surface because the gas detector 10 has a fine structure. In the preferred embodiment, glass wool is used as the dust-free filter 25 so that debris of 0.1 microns or more are prevented from passing therethrough but it does not present any problem for gas to pass therethrough. As is obvious, gas may be introduced into the space as defined by the supporting structure by freely passing through both of the anti-explosion net 24 and dust-free filter 25 to be partly absorbed by the gas detecting semiconductor element 6.

Figure 3:
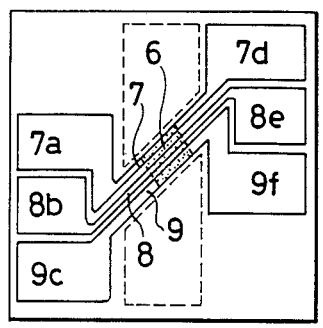
FIG. 3 is a schematic illustration showing the overall structure of the gas detector of FIG. 1 which is useful for explaining its operation.
Figure 4:
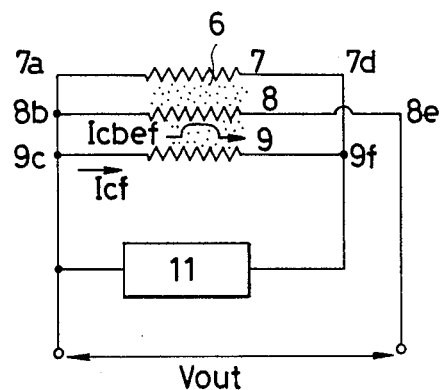
FIG. 4 is a schematic illustration showing the electrical circuit structure of the gas detector of FIG. 1.

With reference to FIGS. 3 and 4, the operation of the gas detector 10 will be described. As mentioned before, the gas detector 10 has three strips extending substantially linearly and arranged side by side. The side strips 7 and 9 serving as heaters are provided with electrode sections 7a, 7d and 9c, 9f, respectively, on both ends, and the center strip 8 is a gas detecting lead which is also provided with a pair of electrode sections 8b and 8e on both ends. As shown in FIG. 4, a voltage supply and pulse driving circuit 11 is connected as shown. Such a sandwiching arrangement in which the gas detecting lead 8 is provided as sandwiched between the side heater strips 7 and 9 one on each side is preferable because temperature may be maintained uniform across the gas detecting semiconductor layer 6. It should be noted, however, that the present invention should not be limited only to such arrangement. As long as uniform distribution of temperature is maintained, various other arrangements may be employed; for example, heater and gas detecting strips may be alternately provided as many as desired.

With a voltage pulse of 1.5–3V applied between the electrode sections 9c and 9f (also between the electrode sections 7a and 7d), current Icf flows, so that the heaters 7 and 9 quickly reaches the temperature ranging from 350° C. to 400° C. in 1–4 milliseconds. As a result, the heat thus produced is transmitted through the insulating film 2 to the gas detecting semiconductor layer 6 thereby causing the layer 6 to be also heated, so that the electrical resistance of layer 6 becomes decreased. When the gas detecting semiconductor layer 6 absorbs a particular kind of gas, its resistance becomes lowered in the order of magnitude by two to three, so that part of the driving current Icf flowing through the heater strip 7 (and 9) flows into the gas detecting strip 8 thereby creating a flow of current Icbef, which may be detected as a change in voltage in the form of a pulse between the electrodes 8b and 8e. Accordingly, the concentration of gas may be detected by observing a change in voltage between the electrodes 8b and 8e.

Figure 5A:
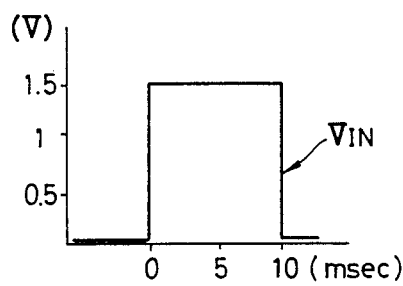
FIGS. 5a and 5b are graphs showing experimental data obtained in the circuit of FIG. 4.
Figure 5B:
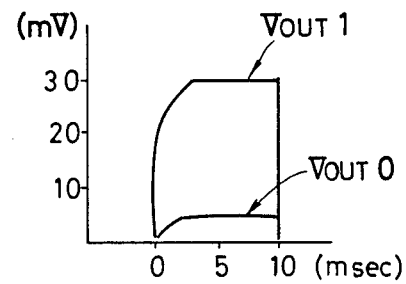

FIGS. 5a and 5b are graphs showing the wave form of an input voltage pulse $V_{IN}$ applied between the electrodes 9c and 9f and the wave forms of resulting output voltage pulses $V_{OUT0}$ for 0% in gas concentration and $V_{OUT1}$ for 0.35% in gas concentration. When a gas of high concentration, e.g., a gas of 100% in concentration is absorbed, Icbef increases and Icf decreases. With a reduction of Idf, there occurs a decrease in temperature in the heater strips 7 and 9, which then causes the temperature of gas detecting semiconductor layer 6 to lower and thus its resistance to increase thereby making Icbef smaller again. Such a belated reduction is preferable because it contributes to shorten the time required for the output voltage at the electrodes 8b and 8e to stabilize and to limit the temperature increase of heater strips 7 and 9. Such an advantage stems partly from the fact that the heater strips 7 and 9 are very small in thermal capacity and thus only a short time period is required for them to reach the thermal equilibrium state and partly from the particular driving scheme employed.

Figure 6:
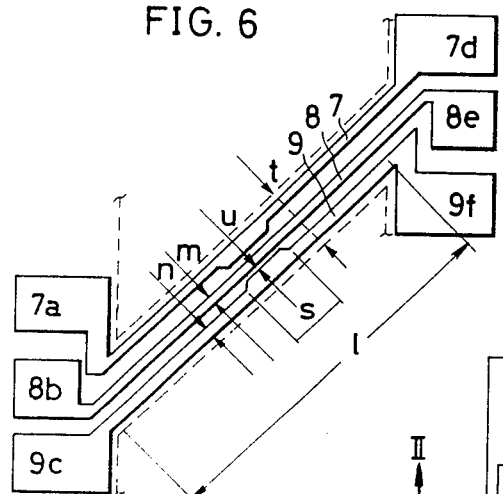
FIG. 6 is an enlarged schematic illustration showing the central portion of the structure shown in FIG. 3.

FIG. 6 is an enlarged view of the pattern of three strips 7–9 shown in FIG. 3. The illustrated strips 7–9 may be preferably dimensioned with l ranging 100 to 500 microns, m ranging from 1 to 3 microns, n ranging from 5 to 20 microns, s ranging from 10 to 50 microns, t ranging from 15 to 50 microns and u ranging from 1 to 3 microns. As may be noticed, the gas detecting strip 8 is narrower with its width m set in the range between 1 and 3 microns. Such a structure is desired so as to improve the S/N ratio of a detecting voltage because the output voltage between the electrodes 8b and 8e may be increased by increasing the resistance of gas detecting center strip 8 and to improve the uniformity of temperature distribution therealong. The electrical resistance of strip 8 between 8b and 8e becomes larger as the width of the strip 8 becomes narrower. Thus, a larger detected voltage signal is obtained for a given detection current as compared with the case in which the strip 8 is wider. It is to be noted that the side heater strips 7 and 9 are provided with widened portions approximately at the midway between the end electrodes. This is so structured as to lower the current density at the central portion where the temperaure tends to be higher than the rest by increasing the cross-sectional area of the strip 8. With such widened portions provided at the center of the heater strips 7 and 9, the heat produced at the central portions of the heater strips 7 and 9 may be reduced by a controlled amount, and as a result the distribution of temperature may be made remarkably uniform along their longitudinal directions. Such a uniform temperature distribution also contributes to prevent the so-called electromigration from occurring, which then contributes to secure an extended service life of heater strips 7 and 9. It should further be noted that the widened portions provided at the center of the heater strips are actually formed by projections projecting inwardly toward the gas detecting strip 8 in the illustrated embodiment. With such a structure, the distance between the side heater strip 7 (and 9) and the center detecting strip 8 is minimized so that the resistance of the gas detecting semiconductor layer 6 presented between the side and center strips 7 (9) and 8 may also be minimized thereby allowing to obtain an increased detecting output voltage between the electrodes 8b and 8e which contributes to enhance its S/N ratio. Such a structure is particularly advantageous because the gas detector 10 may be made less sensitive to humidity and alcohol which are expecially reactive at low temperatures when the distance between the strips 7 and 8 becomes smaller, the overall width t becomes smaller and thus the thermal capacity of the gas detecting semiconductor layer 6 becomes smaller. As a result, the layer 6 can be heated rapidly and thus the time required for the layer 6 to reach a condition for initiation of detection is short.

Accordingly, the time in which noise is produced can be minimized.

Figure 7:
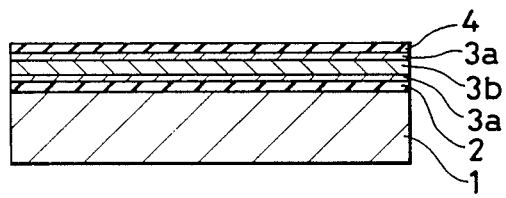

Now, a process for manufacturing the gas detector 10 having the above-described structure in accordance with one embodiment of the present invention will be described with reference to FIGS. 7 through 14. In the first place, as shown in FIG. 7, on a substrate 1 is formed an insulating layer 2, a metal layer 3 and a resist layer 4 in the order mentioned one on top of another. The substrate 1 constitutes a base structure of the gas detector 10 and its supports the strip pattern and the associated electrode pads, and it preferably comprises a material which may be easily subjected to undercut etching without significantly affecting the overlying structure and which does not alter in property as well as in shape at high temperatures, e.g., by heating to 500° C. for a time period of a few to 10 hours. In the present embodiment, use is made of Si (100), but any other material such as Al, Cu, N and Cr may also be used. The substrate 1 illustrated is square in shape, having one side measuring 1–4 mm and a thickness of 0.1–1 mm. It is true though that the substrate 1 is thinner the better because it may be easily split when produced in mass.

The insulating layer 2 is provided to support the strip pattern thereon as electrically isolated from the substrate 1 and to provide electrical insulation between electrically conductive strips. The insulating layer 2 preferably comprises a material which is highly electrically resistive as well as heat-resistant and is similar in thermal expansion coefficient to the heater strip material. For example, such an insulating material may be selected from the group consisting of $Al_2O_3$, MgO, $Si_3N_4$ and $Ta_2O_5$. In the present embodiment, the insulating film 2 is formed for $SiO_2$ by RF sputtering (Ar pressure 0.1–0.01 Torr, input power density 1–10 W/cm$^2$, substrate temperature 350°–400° C.) to the thickness of 0.3–2 microns.

The metal layer 3 in fact has a three-layer structure including underlying and overlying layers 3a, 3a and an intermediate layer 3b sandwiched between these layers 3a, 3a. The underlying layer 3a is provided to increase adherence between the intermediate layer 3b and the insulating layer 2 and it comprises a material which is resistant to both of etchants used to etch the substrate 1 and the insulating layer 2. In the present embodiment, the underlying metal layer 3a is formed from Mo by RF sputtering under the same conditions as described above to the thickness of 300-800 angstroms. Alternatively, other materials such as Cr, Ni and Ti may be used for forming the layer 3a. The intermediate layer 3b will be formed into a heater strip so that it preferably comprises a material which may remain stable in property for an extended period of time. In the present embodiment, the intemediate layer 3b is formed from Pt by RF sputtering under the above-mentioned conditions to the thickness of 0.3-2 microns. As alternatives, such materials as SiC and $TaN_2$ may be used. After formation of the intermediate layer 3b, the overlying contact layer 3a is formed thereon under the same conditions as mentioned above.

The resist layer 4 is formed on top of the three-layer structured metal layer 3 and it serves not only as a mask at the time of dry-etching the metal layer 3 but also as a solder bump glass dam at the time of forming an insulation for the gas detecting strip and a bump in each electrode pad. In the present embodiment, the resist layer 4 is formed from $SiO_2$ by RF sputtering under the above-mentioned conditions to the thickness of 0.5-1 microns.

It is to be noted that the above-described steps may be carried out continuously in the same batch and thus suitable for application to a mass production scheme. When processed continuously, the interface between the two adjacent layers may be maintained clean and thus provides excellent contactability. Moreover, by holding the substrate temperature in the range between 350° and 400° C. during RF sputtering, resulting films may be made more densely thereby allowing to prevent the resistance of metal layer 3 from fluctuating due to aging, and, furthermore, thermal stress produced in the film during operation may be minimized because the operating temperature of gas detector 10 is in the range between 350° and 400° C. Accordingly, reliability in operation is significantly enhanced.

Figure 8:
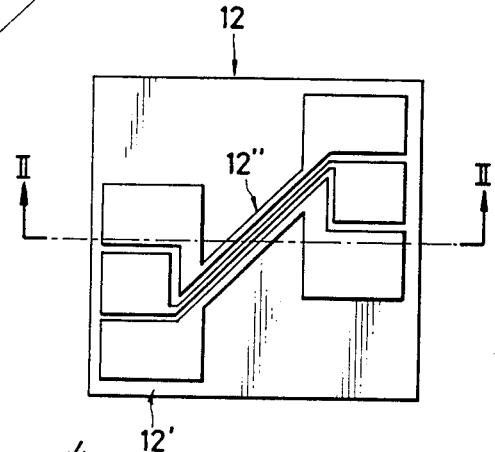

Then the layer 4 of $SiO_2$ is etched by well known photolithographic technology, using common buffered fluoric acid ($HF+NH_4F$) as an etching solution. The photomask to be used includes a pair of parallely arranged heater strip patterns and a gas detecting strip pattern located as sandwiched between the pair of heater strip patterns, each having an elongated section and a pair of electrode sections on both ends of the elongated section. The patterns are determined such that the gas detecting strip may be uniformly heated by the sandwiching side heater strips and that the substrate 1 in the vicinity of the heater strips excepting the electrode pad sections may be undercut when the substrate 1 is subjected to anisotropic etching. FIG. 8 shows an example of such a photomask 12 having desired patterns. Since Si (100) is used as the substrate 1, if the electrode sections 12' are defined on a (111) plane which is difficult to be etched, under a to-be-formed bridge section 12" which is inclined at 45° with respect to the electrode sections 12' located on a (110) plane which is easily etchable. Thus, this (110) plane is undercut when etched thereby forming a void under the to-be-formed bridge section 12". In the case where Si (111) is used as the substrate 1, if the angle formed between the electrode sections 12' and the bridge section 12" in the photomask 12 is set at 15°, then the desired undercutting may be effected.

Figure 9:
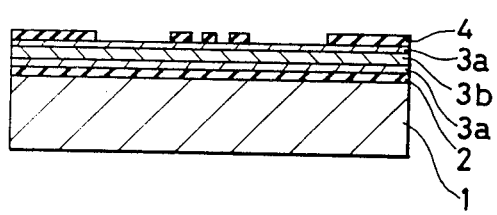
Figure 10:
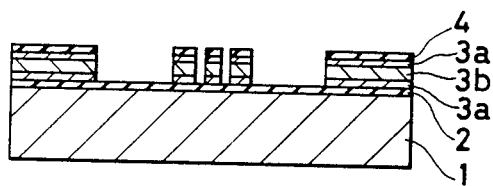
Figure 11:
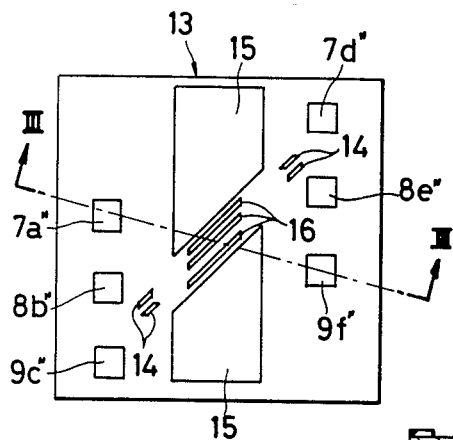
Figure 12:
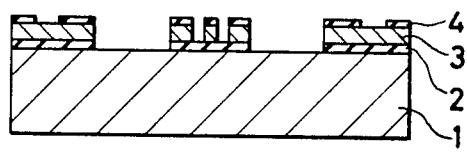

FIG. 9 shows in cross-section the structure taken along line II—II indicated in FIG. 8 after photoetching the $SiO_2$ film 4. After dry-etching the metal layer 3 using the remaining patterned $SiO_2$ film 4 as a mask, the resulting structure is shown in FIG. 10. The use of dry-etching is preferred in this step because Pt is difficult to be wet-etched. Ar sputter etching may be preferably used (Ar pressure 0.1-0.01 Torr, input power density 1-10 W/cm$^2$ and substrate at room temperature); however, any other method such as plasma etching with $CF_4+O_2$ may also be used. Then using a photomask 13 shown in FIG. 11, the $SiO_2$ layers 2 and 4 are selectively etched to define electrode pads using openings 7a", 8b", 9c", 7d", 8e" and 9f" and the substrate 1 is selectively etched using openings 14 and 15. The photomask 13 is also provided with openings 16 for defining a pattern of heater and detector strips. After such photoetching is carried out, the resulting structure taken along line III—III is shown in FIG. 12. As shown, the metal layer 3 in fact has a three layer structure and is comprised of Pt layer 3a sandwiched by a pair of Mo layers at its top and bottom.

Figure 13:
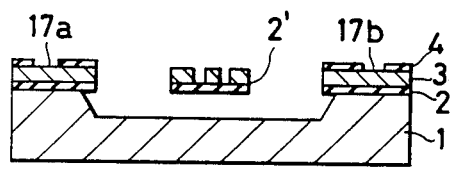

Then using the $SiO_2$ layers 2 and 4 as masks, the Si substrate 1 is subjected to anisotropic etching. As an anisotropic etchant, use may be made of KOH, NaOH (30-60% aqueous solution, liquid temperature 80°-150° C.), APW (ethylenediamine+pyrocatechol+water, liquid temperature 90°-110° C.), hydrazine aqueous solution (64 mol %, liquid temperature 90°-100° C.), etc. As shown in FIG. 13, after etching for 20 to 40 minutes, the substrate 1 below the $SiO_2$ film 2' becomes undercut to the depth of 50 to 300 microns to provide void space thereby forming a profile of bridge structure by the heater and detector strips 7-9. such a bridge structure is defined due to a particular relation between the crystal orientation of the substrate 1 and the pattern of photomask 13. It is to be noted that the openings 14 provided in the photomask 13 of FIG. 11 contribute to provide a sharp edge profile when the substrate is so etched. For example, in the present embodiment, Si (111) tends to remain on both ends of the bridge section during etching; however, the provision of openings 14 help etch these portions effectively so that the etching time may be reduced to half, which in turn contributes to mitigate the damages which might be imparted to the other portions of the structure by the etchant.

If the etched profile is sharp particularly at the ends of the bridge section, there will be less heat conduction from the heater layer 3 to the underlying substrate 1 through the insulating layer 2 so that heating efficiency by the heater strips 7 and 9 may be increased, which then helps to obtain a uniform distribution of temperature especially along the longitudinal direction of the detector strip. The end portions of the bridge section are relatively lower in temperature as compared with the central portion; however, sensitivity to humidity and alcohol may still be maintained low if the gas detecting semiconductor element 6 is formed mostly at the central portion of the bridge section and not on the end portions. FIG. 13 shows the structure which may be obtained after subjecting the structure of FIG. 12 to anisotropic etching thereby causing undercutting preferentially under the bridge section 2'. Then Sn or Au is vapor-deposited to fill the pad holes 17a and 17b to the thickness of few to 10 microns and the substrate 1 is heated to 400°-600° C. to form dome-shaped bumps 5.

Figure 14:
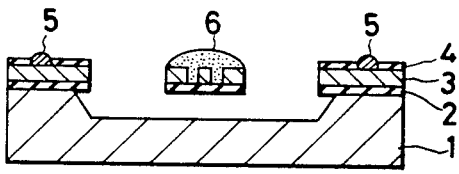

In this instance, making use of the fact that the mask or resist layer 4 of SiO$_2$ defines a pattern of glass dam and is poor in wetability with metal, bumps 5 of Au-Sn eutectic alloy may be formed as dome-shaped as shown in FIG. 14.

In FIG. 14 is shown the semiconductor layer 6 which is provided as filling the gaps between the center and side strips. The semiconductor gas detecting layer 6 may be formed from a metal oxide material such as SnO$_2$, Fe$_2$O$_3$ and ZnO by sputtering, evaporation or the like to the thickness of 0.3–3 microns, or, alternatively, it may be formed by having fine powder of one of the above materials dispersed in a mixture of water and alcohol and applying such a dispersion by spin coating. The process described above requires only two kinds of photomasks and two kinds of evaporation masks and yet accuracy in mask alignment is not so severe and in the order of ±3 microns. As is apparent, the manufacturing process of the present invention is much simpler as compared with the well known IC and LSI processes, so that the present process is low in cost and high in reliability.

Figure 16:
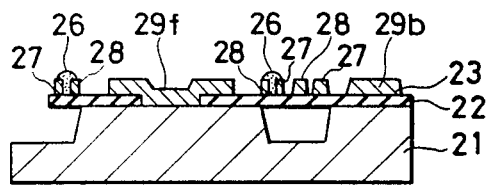
FIGS. 16 and 17 are cross-sectional views taken along lines IV—IV and IV'—IV', respectively, shown in FIG. 15.
Figure 17:
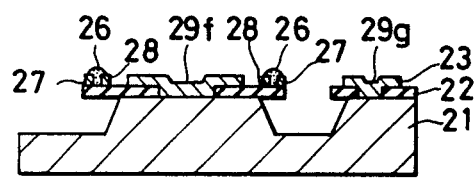

Now, turning to FIG. 15, another embodiment of the present invention will be described in detail. FIGS. 16 and 17 are cross-sectional views taken along lines IV—IV and IV'—IV', respectively. Similarly with the previous embodiment, this gas detector also includes a substrate 21, an insulating layer 22 and a metal layer 23. The metal layer 23 is patterned such that it incldues a disc-shaped electrode 29f, a ring-shaped heater strip 27 of an electrically conductive material which is generally concentric with the disc-shaped electrode 29f and which has one end connected from the disc-shaped electrode 29f and the other end connected to an electrode pad 29b, a ring-shaped detector strip 28 of an electrically conductive material which is generally concentric with the disc-shaped electrode 29f and the ring-shaped heater strip 27 and which has one end connected from the disc-shaped electrode 29f and the other end connected to another electrode pad 29e, and a separate electrode pad 29g. It is to be noted that as shown in FIG. 17, the disc-shaped center electrode 29f is electrically connected to the separate electrode pad 29g through the substrate 1 and via the holes provided in the insulating layer 22.

A gas absorbing semiconductor layer 26 is provided to fill the gap between and on the ring-shaped heater and detector strips 27 and 28. The substrate 21 is undercut around the periphery of the generally disc-shaped insulating layer 22 so that that portion of the insulating layer 22 on which the ring-shaped heater and detector strips 27 and 28 and the semiconductor layer 26 are formed extends into the air, as shown in FIGS. 16 and 17. Of importance, the heater strip 27 is located at a position which is not in contact with and separated away from the substrate 21 also serving as a heat sink as much as possible. As will be understool later, the separate electrode pad 29g is commonly used for heating and detection. The principle of gas detecting operation in the structure of FIG. 15 is substantially identical to that in the case of FIG. 4. In other words, in FIG. 15, a driving voltage pulse is applied between the electrodes 29b and 29f thereby causing the ring-shaped heater strip 27 to be heated, which, in turn, causes the gas detecting semiconductor layer 26 to be heated. As described before, when the semiconductor layer 26 becomes heated, its resistance drops by two to three orders of magnitude, so that the driving current 27 leaks more to the detector strip 28 thereby forming a voltage pulse between the detector electrodes 29b and 29e.

Figure 15:
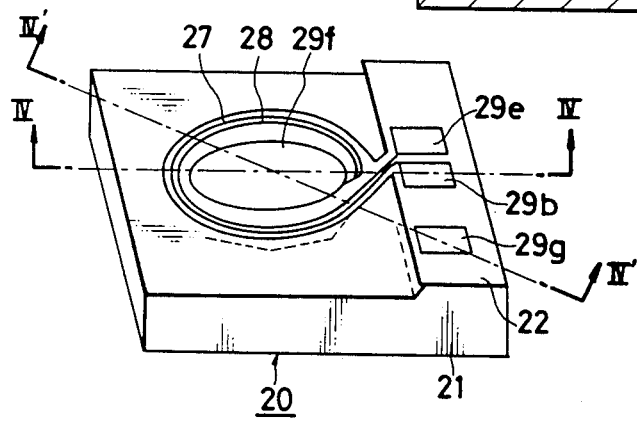
FIG. 15 is a perspective view showing another gas detector constructed in accordance with another embodiment of the present invention.
Figure 18:
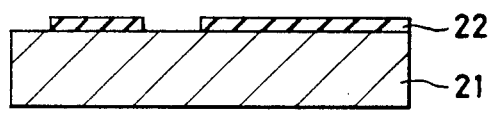
FIGS. 18 and through 21 are cross-sectional views showing the structure at each step in a process for manufacturing the gas detector 20 of FIG. 15.
Figure 19:
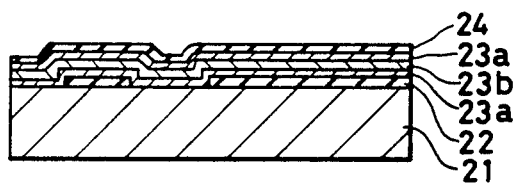
Figure 20:
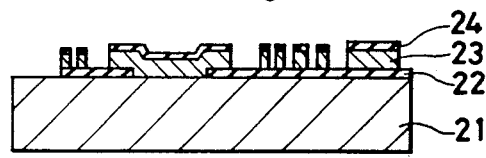
Figure 21:
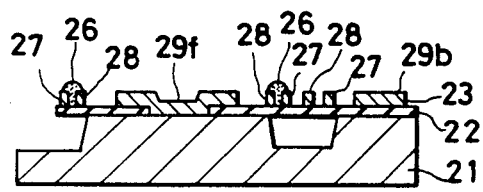

FIGS. 18–21 are cross-sectional views showing the structure at several steps in the process of manufacturing the gas detector of FIG. 15 taken along line IV—IV. As shown in FIG. 18, the insulating layer 22 of SiO$_2$ is formed on the substrate 21 of Si (100) by sputtering. Then using a photomask 14 of FIG. 22, the insulating layer 22 is selectively removed thereby defining an undercut etching opening 22' and contact hole openings 22f and 22g. Then, as shown in FIG. 19, the three layer structure including the sandwiching contact layers 23a of Mo and the sandwiched layer of Pt and the resist or mask layer 24 of SiO$_2$ are formed one after another by sputtering. Then using a photomask 15 of FIG. 23 provided with ring-shaped heater strip pattern 27', ring-shaped detector strip pattern 28', and electrode patterns 29e', 29b', 29f' and 29g', photoetching is carried out to have the mask layer 24 patterned. Then using the thus patterned mask layer 24 as a mask, the composite metal layer 23 having the three layer structure is dry-etched and its resulting structure is shown in FIG. 20.

Then since the patterned mask layer 24 on the composite metal layer 23 is very thin, it is completely removed when dipped into an etchant for SiO$_2$. Thereafter the Si substrate 21 is subjected to anisotropic etching to undercut the substrate 21 around the insulating layer 22 so that the peripheral portion of the insulating layer 22 becomes projected into the air whereby the ring-shaped heater and detector strips 27 and 28 become located on that peripheral portion of the insulating layer 23 whose underside is not adjacent to the substrate 21. Then the semiconductor strip 26 is formed along the ring-shaped heater and detector strips 27 and 28 to provide the structure shown in FIG. 21. In the present embodiment, since the electrodes 29g and 29f are to be electrically connected through the substrate 21, the substrate 21 preferably comprises a material having high electrical conductivity. For example, Si highly doped with an impurity such as B and P may be used, or a metal such as Al, Cu, Ni, Cr, etc. may also be used.

Figure 22:
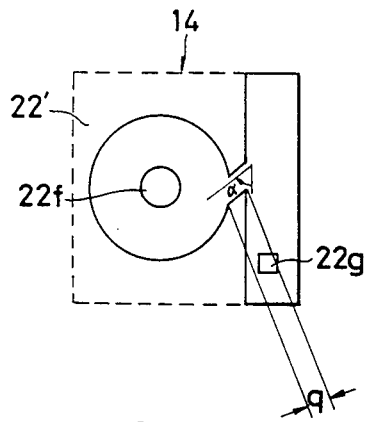
FIGS. 22 and 23 are schematic plan views showing photo-mask patterns used during the process for manufacturing the gas detector 20 of FIG. 15.
Figure 23:
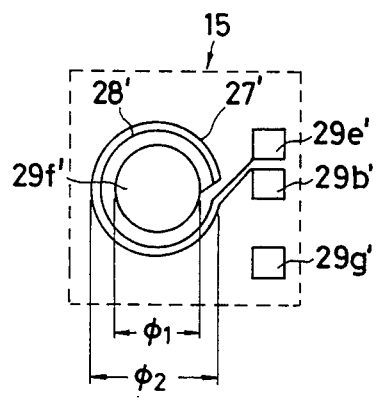

More specifically, the photomasks 14 and 15 shown in FIGS. 22 and 23, respectively, are preferably sized as the diameter $\phi_1$ of disc-shaped electrode 29f' to be 30–800 microns with the ring-shaped detector strip 28' having the width of 1–10 microns located generally concentrically with and radially outside of the disc-shaped electrode 29f' and the ring-shaped heater strip 27' having the width of 3–50 microns located generally concentrically with and radially outside of the ring-shaped detector strip 28'. The gap between the rings 27' and 28' is preferably in the range between 1 and 10 microns. As mentioned earlier, the disc-shaped insulating layer 22 serving as a support for the rings 27' and 28' is also generally concentric with the disc-shaped center electrode 29f' and its diameter is preferably in the range between 50 and 1,000 microns. The ring-shaped strips 27 and 28 are provided wtih respective lead-out portions which are connected to the electrode pads 29e and 29b, respectively. As indicated in FIG. 22, the angle formed between each of the lead-out portions and one side of the square-shaped electrode pad, e.g., 22g, is 45°. This is because, as described with respect to the previous embodiment, such a particular relation between the crystal orientation of Si (100) and the masking pattern allows to have that portion of the substrate 21 which is generally located below the lead-out portions preferentially undercut when subjected to anisotropic etching.

The length q of such a lead-out portion is preferably set at 5-50 microns.

The present embodiment having a generally circular structure is advantageous in obtaining a uniform distribution of temperature. That is, with the provision of the ring-shaped heater strip 27, since heat produced by the heater strip 27 is uniformly directed to its center, there will be more uniformity in temperature distribution as compared with the case of a linear heater strip. Furthermore, the present embodiment is superior in mechanical durability than the liner heater strip type having a bridge-formed supporting structure. This is even more true in the case where the longer heater and detector strips are desired. For example, for the heater strip having the width ranging from 3 to 10 microns and the thickness of 0.3 microns with the valve of resistance at 200 ohms, it must be at least 0.5 mm long. In the case of a straight heater strip, the longer, the higher the influence of thermal expansion. In particular, in the case where the heater strip is driven by pulses, the heater strip will be set in vibration in association with the frequency of application of driving pulses. Such a vibration is disadvantageous because the heater strip may be separated away from the semiconductor layer or cracks may be formed in the insulating layer on which the heater strip is supported. On the other hand, the circularly shaped or coil-shaped heater strip as discussed above does not suffer from these disadvantages since it can absorb thermal expansion.

Figure 24:
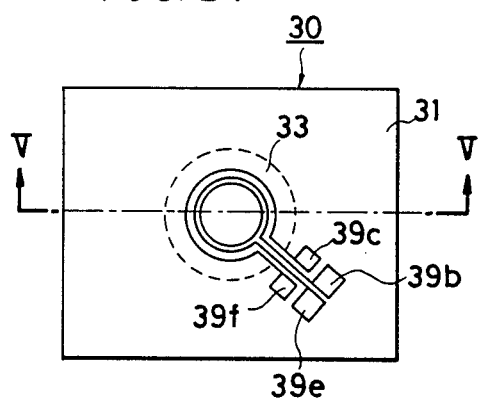
FIG. 24 is a schematic plan view showing a modification of the structure shown in FIG. 15.
Figure 25:
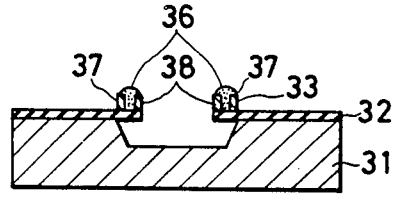
FIG. 25 is a cross-sectional view taken along line V—V shown in FIG. 24.

FIG. 24 shows another embodiment of the present invention which has a ring-shaped heater strip and thus is similar to the embodiment shown in FIG. 15. FIG. 25 is a cross-sectional view taken along line V—V indicated in FIG. 24. As shown, a gas detector 30 in this case includes a substrate 31 which is provided with a circular recess 33 at its center. Such a circularly shaped recess 31 may be provided by subjecting the substrate to an anisotropic etching. On the substrate 31 is formed an insulating layer 32 which is also provided with a circular opening concentrically with the circular recess 33. However, as best shown in FIG. 25, the opening of the insulating layer 32 is smaller in diameter than the circular recess 33 so that the inner peripheral portion of the circular opening defines a projection which extends into the air. On such a projection is formed ring-shaped heater and detector strips 37 and 38 as spaced apart from each other at a predetermined clearance in the radial direction. A gas detecting semiconductor layer 36 is formed along and on on the strips 37 and 38. Also provided are a pair of detector electrode pads 39b and 39e connected on both ends of the detector ring 38 and a pair of heater electrode pads 39c and 39f connected on both ends of the heater ring 37.

Figure 26:
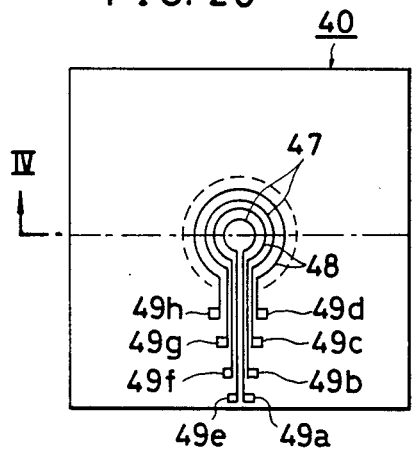
FIG. 26 is a schematic plan view showing a gas detector constructed in accordance with a further embodiment of the present invention.
Figure 27:
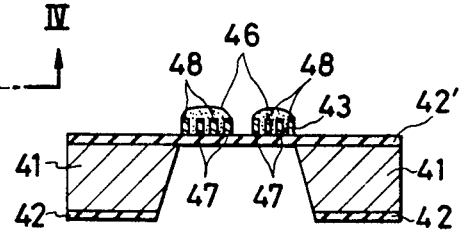
FIG. 27 is a cross-sectional view taken along line VI—VI shown in FIG. 26.

FIG. 26 shows a further embodiment of the present invention and FIG. 27 is a cross-sectional view taken along line IV—IV indicated in FIG. 26. In these figures, 41 is a substrate; 42, 42′ insulating layers; 43 a metal layer; 46 a gas detecting semiconductor layer; 47 ring-shaped heater strips; 48 ring-shaped detector strips; 49a, 49e, 49c and 49g heater electrode pads; 49b, 49f, 49d and 49h detector electrode pads. In fabrication of this device, on both sides of the substrate 41 are first formed insulating layers 42 and 42′, and the bottom insulating layer 42 is patterned to form a center opening through which the substrate 41 is etched until the top insulating layer 42′ is reached. Then the metal layer 43 having the previously described three-layer structure is formed on the top insulating layer 42′ which is then patterned to define ring-shaped heater and detector strips 47 and 48 generally along the inner periphery of the circular recess formed in and through the substrate 41. The electrode pads 49a–49h are defined at the same time. Then the gas detecting semiconductor layer 46 is formed along the ring-shaped strips 47 and 48. In this case, a plurality of the heater and detector rings 47 and 48 (two for each in the illustrated example) are alternately provided concentrically. However, three or more of such rings may also be provided if desired. This embodiment is particularly advantageous because its mechanical durability is very high against the stresses imparted to the insulating layer 42′ due to thermal expansion of the heater rings 47 and externally applied vibrations.

Now, in accordance with another aspect of the present invention, various processes for forming a metal oxide semiconductor film which may be used to define a fine pattern will be described.

Figure 28A:
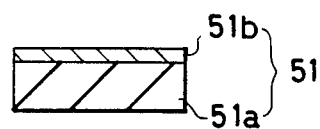
FIGS. 28a through 28h are cross-sectional views showing steps of forming a gas detecting semiconductor film on a heat-resistant substrate in accordance with one method of the present invention.

FIGS. 28a through 28h are cross-sectional views each showing the structure at each step during a process for manufacturing a gas detecting semiconductor film on a heat-resistant substrate in accordance with the present invention. FIG. 28a shows a starting structure and it comprises a substrate 51a of a heat-resistant material such as ceramics and glass and a metal film 51b formed on the substrate 51a from a metal such as $Ta_2N$, SiC, NiCr and Pt by thin film forming technology well known to one skilled in the art. Although not shown specifically, it should be understood that the metal layer 51b has been appropriately patterned and thus heater and detector strips and electrode pads have been already defined. It is to be noted that a combination of the substrate 51a and metal film 51b is also referred to as a "substrate 51" hereinbelow.

Figure 28B:
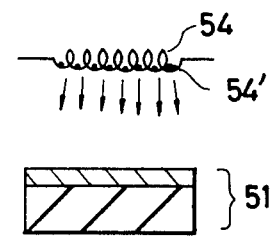
Figure 28C:
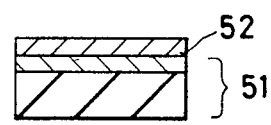

As shown in FIG. 28c, on the substrate 51 is formed a Sn film 52 to the thickness preferably ranging from 0.5 to 3 microns, for example, by evaporation or sputtering. In this instance, if a hydrate of Sn is created in the Sn film 52, the resulting $SnO_2$ film will be too sensitive to humidity so that there will be a lack of stability and reliability when used as an element of a gas detecting device as described above. Furthermore, difficulty will be encountered in converting into a $SnO_2$ film in the later described step of producing a thin film of oxide by thermal decomposition. Accordingly, it is important that no water is contained in or absorbed into the Sn film 52 during its formation. Moreover, since the surface of Sn film 52 is active, it is preferable to make the film 52 dense, and as small in surface area as possible. For example, with the atmosphere inside a vacuum chamber maintained at $1 \times 10^{-6}$ Torr or less and after removing the residual gas and absorbing gas, in particular, $H_2O$ by bake-out or a trap of liquid nitrogen sufficiently, a thin film of Sn is formed by evaporation with the application of heat or sputtering in an Ar atmosphere at pressure ranging from $1 \times 10^{-4}$ to $1 \times 10^{-3}$ Torr. The film forming rate or deposition rate is preferably kept at a relatively slow rate ranging from 0.01 to 0.1 microns/min, thereby allowing to obtain a dense thin film 52 of Sn.

FIG. 28b schematically shows the case in which the Sn film 52 is formed by the resistive heating evaporation method. In this case, an evaporation heater 54 heats tin pellets 54′ to be evaporated and deposited onto the substrate 51.

Figure 28D:
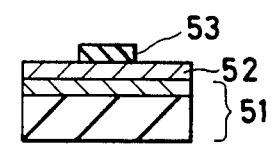

Then, as shown in FIG. 28d, on the Sn film 52 is formed a photoresist 53 which is selectively removed by photolithography thereby forming a desired pattern.

Figure 28E:
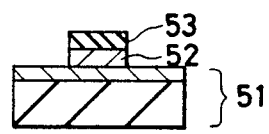
Figure 28F:
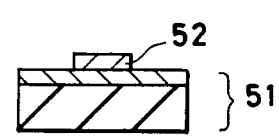

Then, using the thus pattered photoresist 53 as a mask, the Sn film 52 is dipped into an aqueous solution of nitric acid of 2% by volume or more (room temperature) so that the exposed portions of Sn film 52 are converted into white, cotten-like deposits in 10-60 seconds, which are then removed by water washing or ultrasonic cleaning (FIG. 28e). Then the remaining photoresist 53 is removed to provide the Sn film 52 having a desired pattern, as shown in FIG. 28f.

Figure 28G:
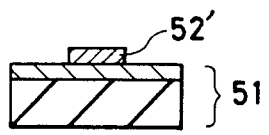
Figure 28H:
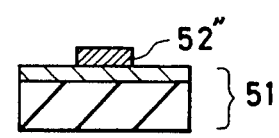

Then the Sn film 52 thus obtained is dipped into an aqueous solution of nitric acid of 0.1-5% by volume (5°-25° C.), which causes to produce white, cotton-like Sn and a film 52' of dilute nitric acid reactant in 0.5-10 minutes (FIG. 28g). These Sn and dilute nitric acid reactant film 52' are then heated to have them thermally decomposed thereby converting the film 52' into an oxide film 52'' of $SnO_2$ (FIG. 28h). The heating may be carried out using an electric furnace which is heated to the temperature ranging from 400° to 600° C. approximately for 1-10 minutes under the atmospheric condition. In this event, if the Sn and dilue nitric acid reactant film 52' on the substrate 51 is observed under illumination by a light source emitting white light, the color changes in the sequence of white-yellow-brown-red-black-white or colorless and transparent as the temperature of the furnace increases. This indicates the sequence of producing the $SnO_2$ film 52'' without containing a hydrate of Sn. The resulting $SnO_2$ film 52'' may be used as a gas detecting element as described previously.

In the above-described process, since patterning may be carried out by photoetching, a gas detecting film having an extremely fine pattern which has not been obtained in the prior art may be obtained with ease and under control. Besides, in the present process, the acid employed is low in concentration, the reaction temperature is low and the processing time is short, so that no corrosion occurs to the material forming the substrate 51, and, thus, the required film may be produced without degrading reliability in operation.

Another process for manufacturing a film of metal oxide semiconductor which is particularly suited for use as a gas detecting film will now be described with reference to FIGS. 29a through 29h. This embodiment is directed to the formation of a gas detecting film on a bridge-formed supporting structure. As described before, such a bridge-formed supporting structure is particularly advantageous because a void space 51c is formed under the supporting layer 51b on which the gas detecting film is to be formed so that the structure can provide a high thermal response and uniform temperature distribution.

Figure 29A:
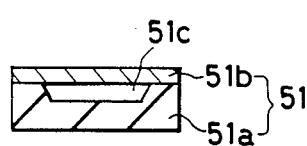
FIGS. 29a through 29h are cross-sectional views showing steps of forming a gas detecting semiconductor film on a bridge structure in accordance with another method of the present invention.

FIG. 29a shows a starting structure in the present process, which includes the substrate 51a and the metal film 51b formed on the substrate 51a. Similarly with the previous embodiment, the metal film 51b is suitably patterned to define heater and detector strips and electrode pads. In this case, however, the substrate 51a is formed with the void space 51c adjacent to the underside of at least part of the metal layer 51b thereby providing a bridge-formed supporting structure. In the present embodiment also, a combination of the substrate 51a and metal layer 51b will be called "substrate 51" hereinbelow.

Figure 29B:
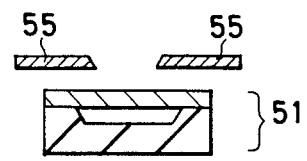
Figure 29C:
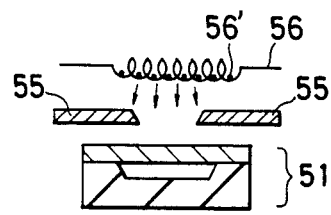
Figure 29D:
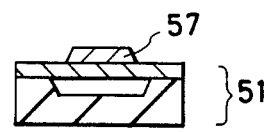

As shown in FIG. 29b, a mask 55 is placed above the substrate 51. The mask 51 has an opening which exposes only a predetermined region of the bridge section and covers the remaining surface of substrate 51 entirely when set in position. Using this mask 55, and Al film 57 having a desired pattern is formed on the substrate 51, a shown in FIG. 29d. FIG. 29c shows the case in which the Al film 57 is formed using the resistive heating evaporation method such that Al pellets 56' are heated by an evaporation heater 56 to be evaporated and deposited onto a predetermined region of the bridge section of substrate 51 through the opening of mask 55. The Al film 57, on the other hand, may also be formed by other evaporation methods or sputtering under the conditions which have beed described with respect to the formation of the Sn film 52 in the previous embodiment.

Figure 29E:
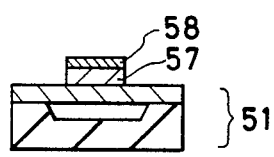
Figure 29F:
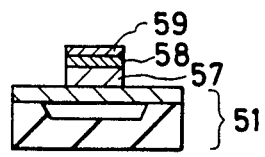

Then, using the mask 55 again, Pt sputtering (Ar pressure $1 \times 10^{-1}$-10 Torr) is carried out to form a porous film 58 of Pt on the Al film 57, as shown in FIG. 29e, to the thickness of 0.02 to 0.06 microns. And, then, using the mask 55 again, Pd sputtering (Ar pressure $1 \times 10^{-1}$-10 Torr) is carried out to form a porous film 59 of Pd on the Pt film 58 to the thickness of 0.02 to 0.06 microns, as shown in FIG. 29f.

Figure 29G:
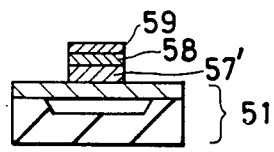
Figure 29H:
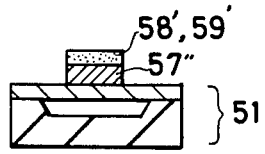

Then, the thus formed Al film 57, Pt film 58 and Pd film 59 are dipped in an aqueous solution of nitric acid of 0.2 to 2% by volume at 5°-25° C., whereby the aqueous solution becomes absorbed into the Pt film 58 and the Pd film 59 through their porous surfaces thereby producing a dilute nitric acid reactant film 57' due to a reaction between the Al film 57 and the impregnated dilute nitric acid, as shown in FIG. 29g. The film 57' formed by a reactant between Al and dilute nitric acid is then heated to have it thermally decomposed thereby producing an oxide film 57'' of $Al_2O_3$. After this thermal decomposition, Pt 58' and Pd 59' are present at the surface of $Al_2O_3$ film 57'' as distributed in dispersion, as shown in FIG. 29h. It is to be noted that the conditions for thermally decomposing the film 57' of a reactant produced from a reaction between Al and dilute nitric acid are the same as described with respect to the formation of the film 52' from a reactant produced from a reaction between Sn and dilute nitric acid.

The gas detecting semiconductor film thus produced may be generally categorized in the so-called contact combustion type catalyst. However, as differnt from the prior art catalyst, since the present film is produced by thin film forming technology, an extremely fine pattern may be obtained. Moreover, the resulting film is stable as a catalyst for an extended period of time because the $Al_2O_3$ film 57'' obtained from the thermal decomposition of the Al-dilute nitric acid reactant film 57' is thermally quite stable and capable of holding Pt 58' and Pd 59' in position strongly.

It is to be noted that the present film forming method may be advantageously applied to the formation of a transparent electrode film which is often required in a device such as a liquid crystal display panel and a plasma display panel. Thus, as a further embodiment of the present invention, there will be described a process for forming a transparent electrode film of tin oxide on the surface of a glass substrate with reference to FIGS. 30a through 30g.

Figure 30A:
FIGS. 30a through 30g are cross-sectional views showing steps of forming a transparent electrode film in a liquid crystal display panel in accordance with a further method of the present invention.
Figure 30B:
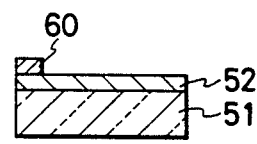
Figure 30C:
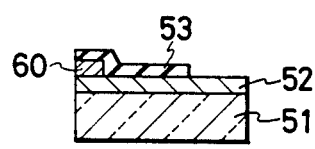
Figure 30D:
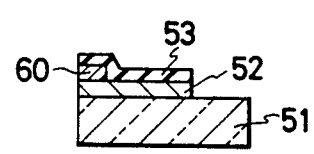
Figure 30E:
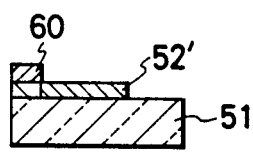
Figure 30F:
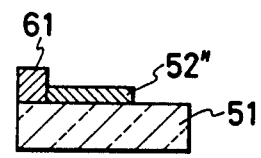
Figure 30G:
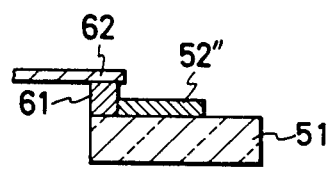

At the outset, as shown in FIG. 30a, the thin film 52 of Sn is formed on the substrate 51 which is glass in the present embodiment. Then, as shown in FIG. 30b, a film 60 of Au is selectively formed in a predetermined region on the Sn film 52 using a mask in the well known thin film forming technology. Then, as shown in FIG. 30c, the photoresist 53 is formed covering the Au film 60 and Sn film 52, which is then patterned using the well known photolithographic technology. Then, as shown in FIG. 30d, undesired portions of Sn film 52 are removed, which is followed by the step of removing the remaining photoresist 53 entirely from the structure using a resist separating agent. Then the remaining Sn film 52 is dipped into an aqueous solution of nitric acid thereby producing the film 52' which is formed by a reactant from a reaction between Sn and dilute nitric acid, as shown in FIG. 30e. Then with the application of heat, the film 52' is thermally decomposed to produce the film 52" and $SnO_2$, as shown in FIG. 30f. In this instance, since the underlying portion below the Au film 60 does not come into contact with the aqueous solution of nitric acid, it remains as Sn but it reacts with the Au film 60 during the step of thermal decomposition, thereby forming an eutectic alloy 61 of Au - Sn system conveniently. such an Au - Sn system eutectic alloy 61 may be used as a bump for thermocompression bonding, so that a lead 62 may be thermocompression-bonded to the bump 61, as shown in FIG. 30g.

It is to be noted that the films 52, 52' and 52" in the present embodiment may be formed as in the manner described with respect to the previous embodiment of forming a gas detecting semiconductor film on a heat-resistant substrate. It is to be noted that in accordance with the present invention a transparent electrode film is formed by photoetching so that a very fine pattern may be defined with ease and bonding may be carried out securely as well as easily. For example, in the prior art liquid crystal display panel, a connection to its transparent electrode film from a driving circuit is made by an electrically conductive rubber contact. On the other hand, in accordance with this aspect of the present invention, such a connection may be made by wire bonding thereby allowing to increase reliability in operation.

Figure 31:
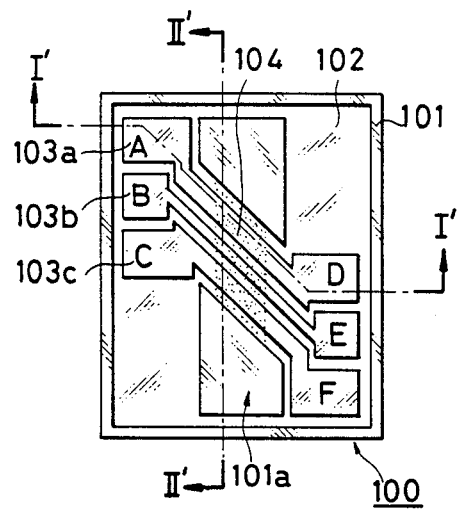
FIG. 31 is a plan view showing a gas detector constructed in accordance with a still further embodiment of the present invention.
Figure 32:
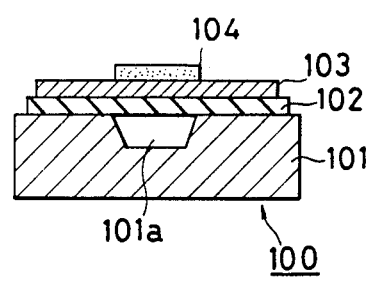
FIG. 32 is a cross-sectional view taken along line I'—I' shown in FIG. 31.

FIG. 31 shows the overall structure of a minute sized gas detector 100 employing a micro-heater. FIG. 32 is a cross-sectional view taken along line I'—I' indicated in FIG. 31. As shown, on a substrate 101 is formed an insulating layer 102 on which is also formed a metal layer 103, which is patterned to define three separate strips 103a, 103b and 103c each provided with electrode sections (A-F) on both ends. The substrate 100 is provided with a rectangularly shaped recess 101a located generally centrally at its top surface, thereby defining a bridge-like structure. Furthermore, a gas detecting layer 104 is formed partly covering the three strips 103a–103c as shown. Among the three strips, the side strips 103a and 103c are heater strips, which produce head due to Joule heating when an electric current is passed therethrough, and the center strip 103b is a detector strip for producing a detection signal indicating the presence or overpresence of a particular gas to be detected.

Figure 33:
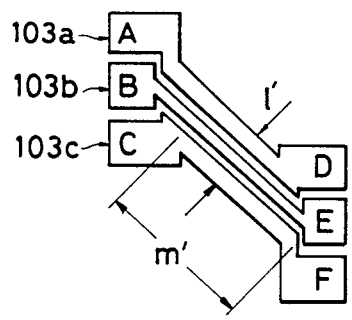
FIG. 33 is a schematic illustration showing part of the structure shown in FIG. 31.
Figure 34:
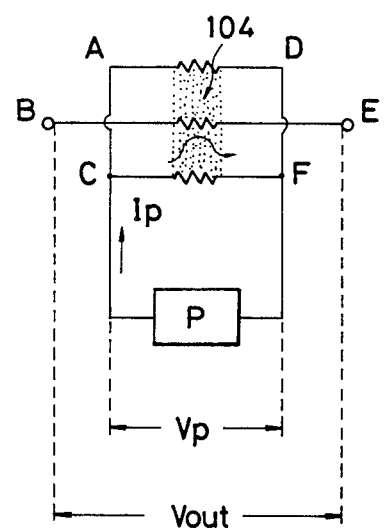
FIG. 34 is an electrical circuit structure of the gas detector shown in FIG. 31.

As shown in FIG. 33, the bridge section extending above the void space 101a formed in the substrate 101 has dimensions such that l=40 microns, m=500 microns and the area of bridge section=$2 \times 10^4$ microns squared. FIG. 34 shows a driving circuit which may be used to drive the gas detector 100. When a voltage pulse is applied from a source P between the electrodes A and D and C and F, the gas detecting layer 104 becomes heated by the heater strips 103a and 103c so that the value of its electrical resistance lowers. When the gas detecting layer 104 absorbs a gas, the value of its resistance drops by 2 to 3 orders of magnitude, and, as a result, the current passing through the heater strips 103a and 103c is partly by-passed into the center detector strip 103b. Therefore, the concentration of gas may be detected by observing the changes in voltage between the electrodes B and E. In the circuit of FIG. 34, if the resistances between electrodes A and C and D and F are both such that $R_0=56$ ohms at room temperature, then it will be R=77 ohms ($R/R_0=1.38$) for $I_P=22$ mA and $V_P=1.7V$, so that approximately 37 mW of power will be consumed.

Figure 35:
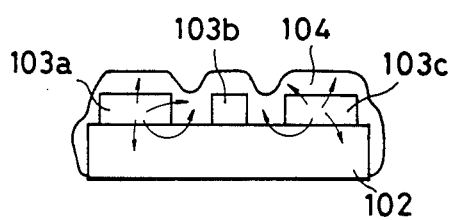
FIG. 35 is a cross-sectional view taken along line II'—II' shown in FIG. 31.
Figure 36:
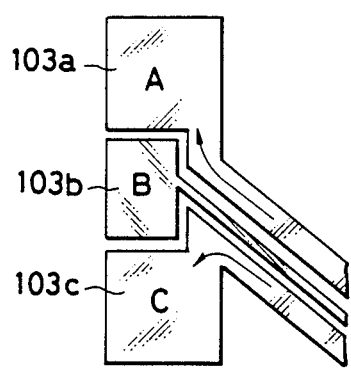
FIG. 36 is a schematic illustration showing part of heater sections on an enlarged scale useful for explaining the manner of heat dissipation.

FIG. 35 is a cross-sectional view taken along line II'-II' indicated in FIG. 31 and shown on an enlarged scale schematically. In FIG. 35, heat conduction from the heater strips 103a and 103c is indicated by the arrows, and it will be appreciated that the temperature of heated gas detecting layer 104 will not be uniform especially in the traverse direction. Disadvantages such as inefficient heating, a reduction in gas absorption and difficulty in preferential detection of a particular gas may be brought about. Moreover, as shown in FIG. 36, in which the directions of heat conduction in the side heater strips 103a and 103c are indicated by the arrows, the heat produced at the central portions of the heater strips 103a and 103c partly escape to the electrode sections A and C, thereby causing power loss in heating. This is because, each of the electrode sections A and C is normally formed to have a surface area which is significantly larger than the surface area of the bridge section and in contact with the substrate 101 which functions as a heat sink. Furthrmore, the heater strips 103a and 103c are formed from a metal material having a relatively larger thermal conductivity.

Figure 37:
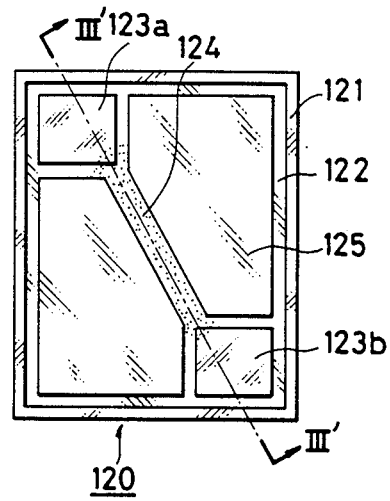
FIG. 37 is a schematic plan view showing a gas detector constructed in accordance with a still further embodiment of the present invention.
Figure 38:
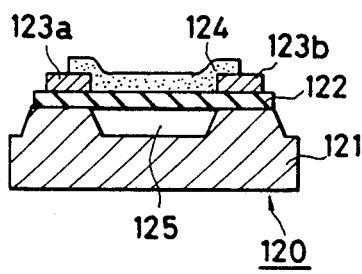
FIG. 38 is a cross-sectional view taken along line III'—III' shown in FIG. 37.

Now, a gas detector constructed in accordance with a further embodiment of the present invention which is free of the above-described problems will be described below. FIG. 37 shows in plan view an improved gas detector 120 and FIG. 38 is a cross-sectional view taken along line III'—III' indicated in FIG. 37. This gas detector 120 includes a substrate 121 provided with a generally rectangularly shaped void space 125 and an insulating layer 122 having a pair of base sections formed on the corresponding ridges of substrate 121 and an elongated section extending between the base sections thereby forming a bridge-shaped structure. On each of the base sections is formed an electrode section or pad 123a or 123b. On the elongated section defining the bridge-shaped structure is formed a gas detecting layer 124 as extending between the electrode sections 123a and 123b. The substrate 121 is formed from a material which is heat-resistant and which may be easily undercut during etching without causing any damages to the overlying structure.

The preferred materials for substrate 121 include Si, Cr, Ni, Mo, NiCr and stainless steel. The substrate 121 preferably has the thickness ranging from 0.1 to 1 mm. The insulating layer 122 is formed from a material which is highly heat-resistant and electrically insulating, such as $Si_3N_4$, $SiO_2$, $SnO_2$, $TiO_2$, $Ta_2O_5$, MgO, $Al_2O_3$ and $ZrO_2$, to the thickness of 0.5-5 microns. The electrode sections 123a and 123b are formed from a material having a high electrical conductivity, such as Ti, Ni, Cr, NiCr, Au, Pt, Rh, W, Mo, a metal carbide like WC, a metal silicide like PtSi and a metal nitride like $Ta_2N$, to the thickness of 0.5-5 microns. The gas detecting layer 124 is formed from a metal oxide semiconductor material, such as $SnO_2$, $Fe_2O_3$ and ZnO, to the thickness of 0.5-5 microns.

Figure 39:
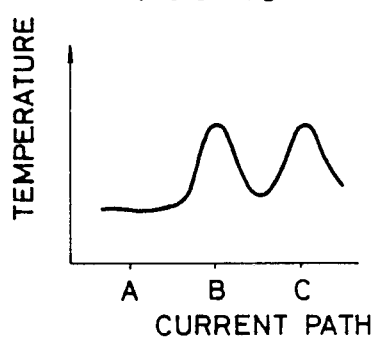
FIG. 39 is a schematic illustration which is useful for explaining the principle of operation of some embodiments of the present invention.
Figure 40:
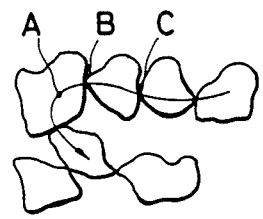
FIG. 40 is a graph showing the characteristic obtained along the current path indicated by the solid line in FIG. 39.

It will now be described as to the principle of operation of the gas detecting device 120 shown in FIG. 37. It is to be noted that the metal oxide semiconductor forming the gas detecting layer 124 is in fact comprised of a collection of fine particles as schematically indicated in FIG. 39. Observed microscopically, contact points or area between the adjacent particles are small so that the contact resistance is relatively large. As a result, when current is passed through this layer 124, more Joule heating takes place at the contact points between the particles rather than at the bulk of each of the particles. The temperature distribution along the current path indicated in FIG. 39 is graphically shown in FIG. 40, in which the abscissa is taken for the current path and the ordinate is taken for temperature. The locations indicated by A, B and C on the abscissa correspond to the locations A, B and C, respectively, shown in FIG. 39. It is shown in FIG. 40 that the temperature is higher at contact points between particles than at the bulk of each particle. As described before, the gas detecting layer 124 is formed on the bridge-shaped insulating layer 122 which extends above the void space 125 provided at the top surface of the substrate 121, and, moreover, it is extremely small in thermal capacity due to its minuteness in structure, so that it is easily self-heated to a desired temperature level sufficient for absorption of gas.

Figure 41:
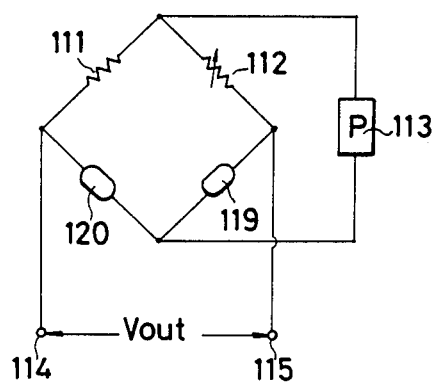
FIG. 41 is a circuit diagram showing the driving circuit which may be used with the present gas detector.

FIG. 41 shows an example of a driving circuit which may be advantageously applied to drive the gas detecting device 120 of FIG. 37. As shown, the gas detector 120 is connected as a detecting element in the form of a well known bridge circuit. The driving circuit also includes a temperature compensating element 119 which is, in fact, comprised of the same gas detector 120 as completely enclosed, a resistor 111 and a variable resistor 112. The driving circuit receives power from a source such as a battery or a pulse generator, and changes in output voltage $V_{OUT}$ between terminals 114 and 115 are monitored to detect presence or overpresence of gas. Since the gas detector 120 is susceptible to changes in the sorrounding atmospheric temperature, it is preferable to be driven by a bridge-formed driving circuit as shown in FIG. 41.

With the area of the gas detecting layer 124 shown in FIG. 37 equal to the total area of the heater strips on the bridge section shown in FIG. 33, if the driving voltage for the gas detector 120 is 1.7V, then the value of current is 0.5 mA and the power consumption is 0.85 mW. In accordance with the present invention, since the size may be reduced more without problem, for example a gas detector whose area of gas detecting layer is in the order of 1 micron squared, a further reduction of power consumption is possible as the device is made smaller. Besides, under the condition, if the gas detector 120 is used as a gas leak alarm in combination with the driving circuit of FIG. 41, an increase of 10 mV in output voltage for the presence of 0.4% of isobutane in the atmosphere as compared with the atmosphere having no isobutane, which indicates sufficient ability of gas detection. In comparison, in the gas detection 100 of FIG. 31, the driving current is 22 mA and the power consumption is 37 mW. As a result, the structure shown in FIG. 37 is more advantageous and highly efficient because the driving current and power consumption may be reduced to ¼ and 1/40, respectively, as compared with the structure of FIG. 31. This is believed to be based on the phenomenon of the temperature being higher at the contact points between the adjacent particles where the effect of gas absorption is higher in the metal oxide semiconductor film serving as a gas detecting film, and, thus, the input power may be reduced since it may be avoided to heat the bulk of each of the particles which does not participate so much in absorption of gas. In addition, the temperature of the bridge section as a whole is not increased significantly and thus there will be less aging effects.

Figure 42:
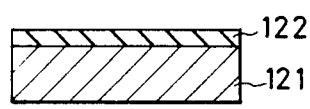
FIGS. 42 through 48 are cross-sectional views showing steps of one process of manufacturing the gas detector of FIG. 37 in accordance with a still further embodiment of the present invention.
Figure 43:
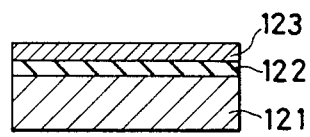
Figure 44:
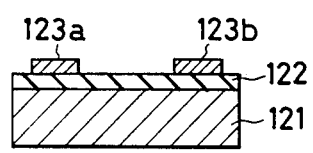
Figure 45:
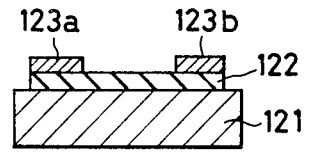
Figure 46:
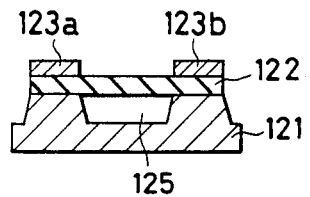

Now, a process for manufacturing the gas detector 120 will be described with reference to FIGS. 42-48. In the first place, on the substrate 121 is formed the insulating layer 122 using the well known film forming technology such as evaporation, sputtering and CVD (FIG. 42). Then on the insulating layer 122 is formed the electrode layer 123, for example, by evaporation or sputtering (FIG. 43). Thereafter, using the well know photolithography, the electrode layer 123 is selectively removed to define the electrode sections 123a and 123b (FIG. 44). For example, if the electrode layer 123 is formed from Ti, then the layer 123 may be selectively etched by an aqueous solution of 20–50% HF (liquid temperature 30°–35° C.) for 0.5–5 minutes using photoresist as a mask. Furthermore, the insulating layer 122 is patterned by photolithography (FIG. 45). The thus patterned insulating layer 122 has a pattern which may be used as a mask in forming the void space 125 by etching the substrate 121 and as a supporting bridge structure for supporting thereon the gas detecting layer 124. That is, if the substrate 121 is Si (100), then it is so selected that the end of the supporting bridge structure is at 45° with respect to the Si (111) plane of the substrate 121 in order that the void space 125 may be formed under the insulating layer 122 by applying the well known anisotropic etching. If the insulating layer 122 is SiO$_2$, it may be etched by buffered fluoric acid liquid (liquid temperature 30°–40° C.) using photoresist as a mask for 1–10 minutes.

Figure 47:
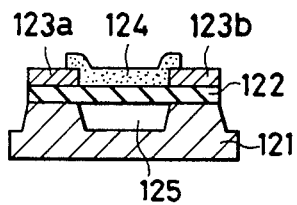
Figure 48:
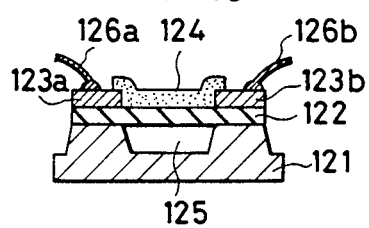

Then, using the patterned insulating layer 122 as a mask, the substrate 121 is subjected to anisotropic etching to form the void space 125 (FIG. 46) to the depth ranging from 20 to 100 microns. For example, if the substrate 121 is Si, use may be made of such anisotropic etching liquid as ethylenediamine+catechol +water (liquid temperature 90°–120° C.) and an aqueous solution of 20–70% NaOH (liquid temperature 80°–130° C.). Then the gas detecting film 124 is formed on the insulating layer 122 defining a supporting bridge structure. The film 124 is formed long enough to contact or partly overlap each of the electrode sections 123a and 123b on both ends (FIG. 47). The formation of film 124 may be carried out for example by deposition of a metal oxide semiconductor material by evaporation or sputtering through an opening defined in a metal mask. Finally, leads 126a and 126b are connected to the electrode sections 123a and 123b, respectively, to complete the gas detector (FIG. 48).

Figure 49:
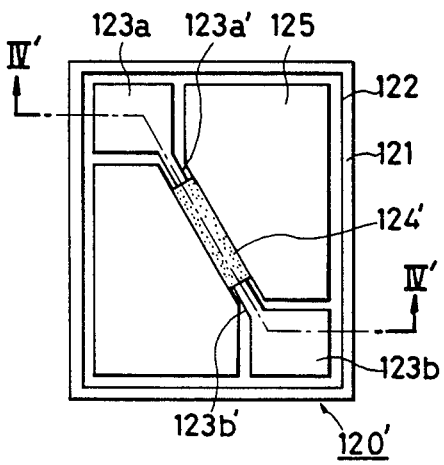
FIG. 49 is a schematic plan view showing a gas detector constructed in accordance with a still further embodiment of the present invention.
Figure 50:
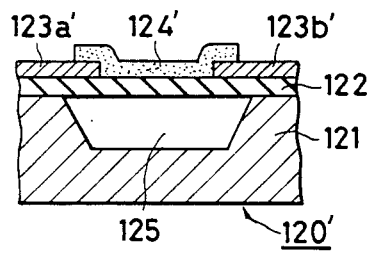
FIG. 50 is a cross-sectional view taken along line IV'—IV' shown in FIG. 49.

FIG. 49 illustrates a gas detector 120' constructed by modifying the above-described embodiment. FIG. 50 is a cross-sectional view taken along line IV'—IV' indicated in FIG. 49. The gas detector 120' is structurally similar to the gas detector 120 shown in FIGS. 37 and 38 in many respects. In the present embodiment, however, the connection between the gas detecting film 124' and each of the electrode sections 123a and 123b is defined at a position on the supporting bridge section. As a result, in the gas detector 120', elongated leads 123a' and 123b' extend along the bridge section from the electrode sections 123a and 123b, respectively. Such a structure contributes to enhance uniformity of the temperature distribution in the gas detecting film 124', which then increases selectivity in the kinds of gas to be detected at a particular temperature.

Figure 51:
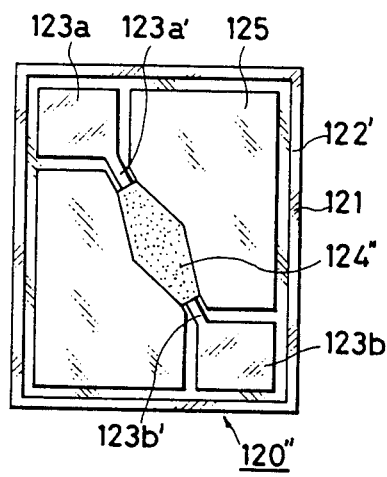
FIG. 51 is a schematic plan view showing a gas detector constructed in accordance with a still further embodiment of the present invention.

A further modification of the above-described embodiment is illustrated in FIG. 51. As shown, in a gas detector 120'', the bridge section is not straight but it is made wider toward the center, where the temperature tends to be higher along the lengthwise direction. With such a structure, the temperature distribution in the gas detecting film 124'' may be made even more uniform. In addition, since the current density may be made smaller at the location where the temperature tends to be higher, no deterioration in performance will occur and thus service life may be extended.

Figure 52:
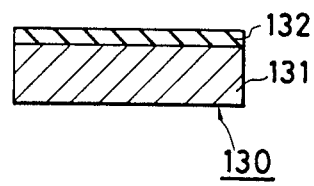
FIGS. 52 through 56 are cross-sectional views showing steps of a process of manufacturing a still further embodiment of the present gas detector.
Figure 54:
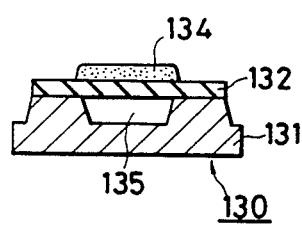
Figure 53:
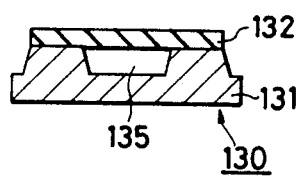
Figure 55:
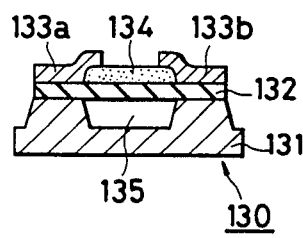
Figure 56:
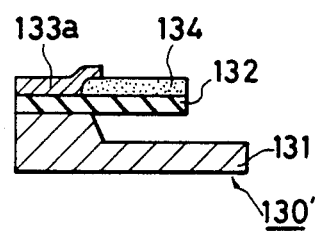

FIGS. 52 through 55 show cross-sectional views at several steps in another process for manufacturing a gas detector 130. As shown in FIG. 52, an insulating layer 132 is first formed on a substrate 131. Then the insulating layer 132 is suitably patterned and then using the thus patterned insulating layer the substrate 131 is selectively etched to form a void space 135 thereby defining a bridge structure by the patterned insulating layer 132. Then, using metal mask, a gas detecting film 134 is formed on the bridge-formed insulating layer 132 from a metal oxide semiconductor material by evaporation or sputtering. Then, using another metal mask, electrode sections 133a and 133b are formed. In the above-described process for manufacturing the gas detector 130, no etching is required to form the electrode sections 133a and 133b so that the process is simplified. It is to be noted that as a modification of the structure shown in FIG. 55, the bridge section may be formed as a cantilever structure as illustrated in FIG. 56.

Figure 57:
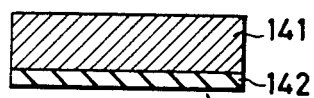
FIGS. 57 through 59 are cross-sectional views showing steps of a process of manufacturing a still further embodiment of the present gas detector.
Figure 58:
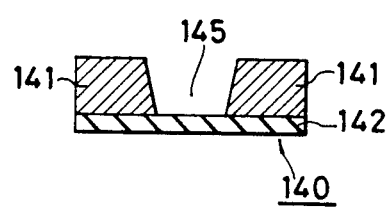
Figure 59:
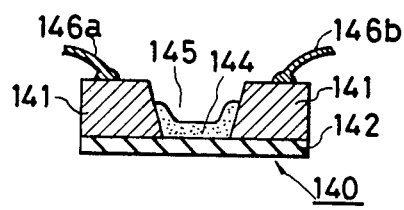
Figure 60:
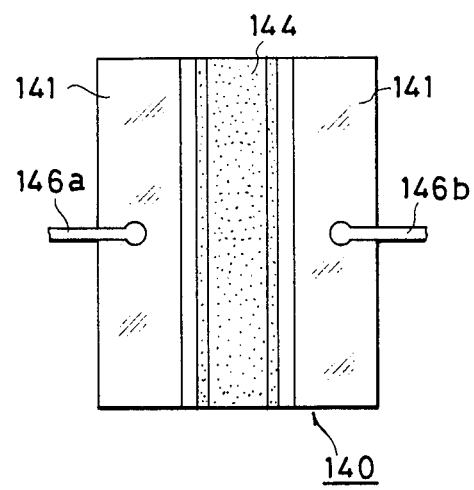
FIG. 60 is a plan view of the gas detector shown in FIG. 59.

FIGS. 57 through 60 show cross-sectional views at several steps in a further process for manufacturing a sill further embodiment, gas detector 140, of the present invention. The gas detector 140 includes a substrate 141 which is formed from an electrically conductive material. As shown in FIG. 57, an insulating layer 142 is formed at the bottom of the substrate 141. Then the substrate is selectively etched until the insulating layer 142 is reached to define a void space 145 in the substrate 141. Thereafter, using a metal mask, a gas detecting film 144 is formed on the insulating layer 142 within the void space 145 from a metal oxide semiconductor material. As an alternative, after drying, baking and grinding a neutralized sediment of tin chloride, the resulting powder is dispered in an organic solvent, which may be applied to the interior of the void space 145 to form the gas detecting film 144. In the case, since the substrate 141 is electrically conductive, there is no need to form separate electrode sections and leads 146a and 146b may be directly connected to desired portions of the substrate 141. FIG. 60 is a plan view of the gas detector 140 shown in FIG. 59.

Figure 61:
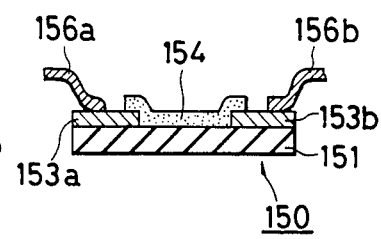
FIG. 61 is a cross-sectional view showing a still further embodiment of the present gas detector.

FIG. 61 illustrates a still further embodiment, gas detector 150, of the present invention. The gas detector 150 includes a substrate 151 which is comprised of an electrically insulating material, such as glass, $SiO_2$, $Al_2O_3$, and MgO, or a highly heat-resistant film as fluoroplastics, polyimid, epoxy resin, and silicon resin, and extremely thin in the order of 0.01-1 mm. On top of the substrate 151 is formed electrodes 153a and 153b and a gas detecting film 154 with leads 156a and 156b connected to the electrode 153a and 153b, respectively. In this embodiment, since the gas detector 150 employs the extremely thin substrate 151 which is electrically insulating and small in thermal capacity, steps of photoetching of the insulating layer 122 and undercutting of the substrate 121 in the case of the gas detector 120 shown in FIGS. 37 and 38 need not be carried out.

Figure 62:
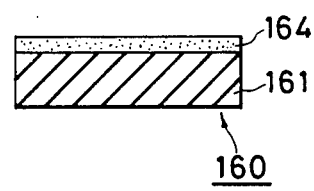
FIGS. 62 through 66 are cross-sectional views showing steps of a process of manufacturing a still further embodiment of the present gas detector.
Figure 63:
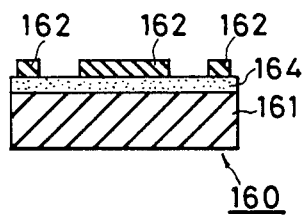
Figure 64:
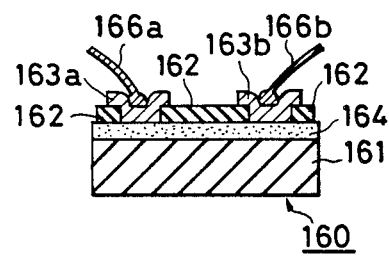
Figure 65:
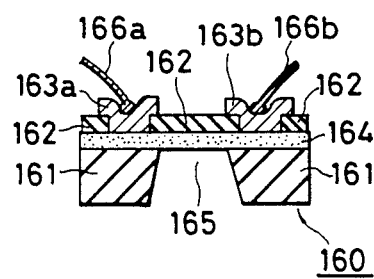
Figure 66:
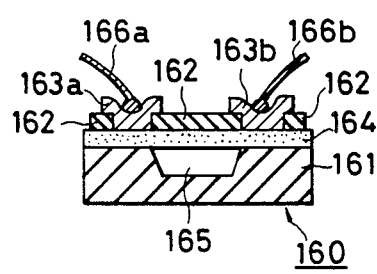
Figure 67:
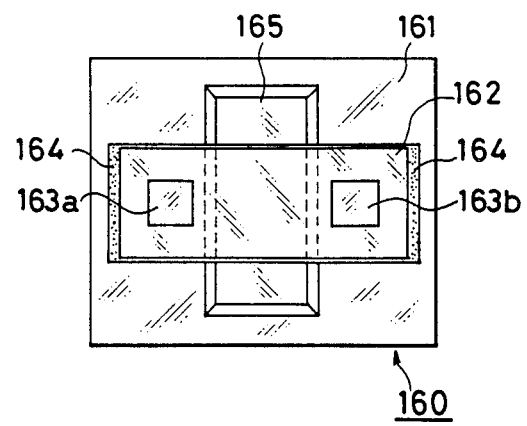
FIG. 67 is a plan view of the gas detector shown in FIG. 66.

FIGS. 62 through 67 are cross-sectional views at several steps for manufacturing a even still further embodiment, gas detector 160, of the present invention. As shown in FIG. 62, at the outset, a gas detecting layer 174 is formed on an electrically insulating substrate 161 of ceramics, highly heat-resistant resin, etc. The gas detecting layer 164 may be formed, for example, from a metal oxide semiconductor material by evaporation, sputtering, CVD, or the like to a desired pattern to the thickness of 0.5-5 microns. As an alternative, after processing through the well known wet process, the layer 164 may be formed by screen printing or spin coating. Then using a metal mask an insulating layer 162 is formed by evaporation, sputtering or the like and then it is selectively etched to define a pair of openings. Then using a metal mask electrodes 163a and 163b are formed as partly filled in the respective openings and leads 166a and 166b are bonded to the electrodes 163a and 163b, respectively. Furthermore, in the case where the substrate 161 has a thickness which is larger by ten times or more than the gas detecting layer 164, undercutting is carried out, as shown in FIG. 65 or 66, to form a void space 165 thereby allowing to reduce power consumption. FIG. 67 is a plan view of the gas detector 160.

Figure 68:
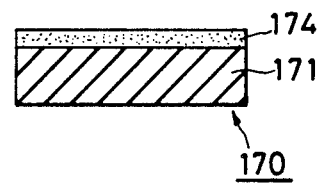
FIGS. 68 through 70 are cross-sectional views showing steps of a process of manufacturing a still further embodiment of the present gas detector.
Figure 69:
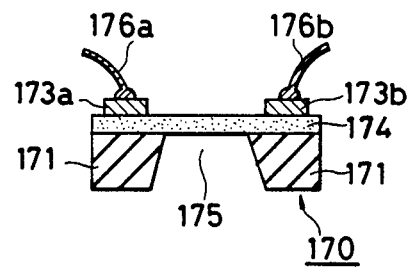
Figure 70:
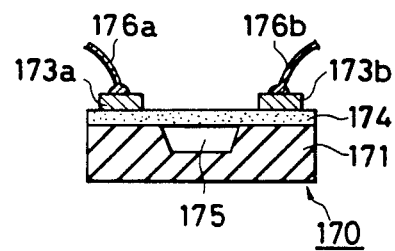

FIGS. 68 through 70 are cross-sectional views at several steps of a still further process for fabricating a still further embodiment, gas detector 170, of the present invention. In the first place, a gas detecting layer 174 is formed on an electrically insulating substrate 171. For example, the gas detecting layer 174 is formed from a metal oxide semiconductor material to the thickness of 5-100 microns. Then the substrate 171 is subjected to undercut etching to form a void space 175 as shown in FIGS. 69 or 70. On the other hand, on the gas detecting layer 174 is formed a pair of electrodes 173a and 173b by evaporation, sputtering or the like using a metal mask, and then leads 176a and 176b are bonded to the electrodes 173a and 173b, respectively. It is to be noted that in the present embodiment the gas detecting layer 174 defines a bridge structure by itself. Thus, the gas detecting layer 174 in this case preferably has the thickness raging from 5 to 100 microns in order to have a sufficient mechanical strength against externally applied forces and vibrations. However, its upper limit in thickness should be determined by power consumption because the thicker the gas detecting layer 174, the larger the power consumption. Alternatively, the mechanical strength of gas detecting layer 174 may be increased by having a binder, such as silica and alumina, mixed with a metal oxide semiconductor material when forming the gas detecting layer 174.

What is claimed is:

1. A method for manufacturing a film of metal oxide comprising the steps of:
    forming a thin film of metal on a substrate;
    reacting said thin film of metal with a dilute nitric acid thereby converting the film into a first film of a reactant produced in a reaction between said metal and said dilute nitric acid; and
    thermally decomposing said first film thereby converting said first film into a film of a metal oxide which is produced during the thermal decomposition.

2. A method of claim 1 wherein said metal comprises Sn.

3. A method of claim 1 wherein said metal comprises Al.

4. A method of claim 2 wherein said metal oxide film is a gas detecting film which changes its electrical resistance when it absorbs a gas.

5. A method of claim 2 wherein said metal oxide film is a transparent electrode film.

6. A method of claim 3 further comprising the step of depositing Pt and Pd onto said film of metal prior to the step of reacting.

* * * * *